Figure 1:
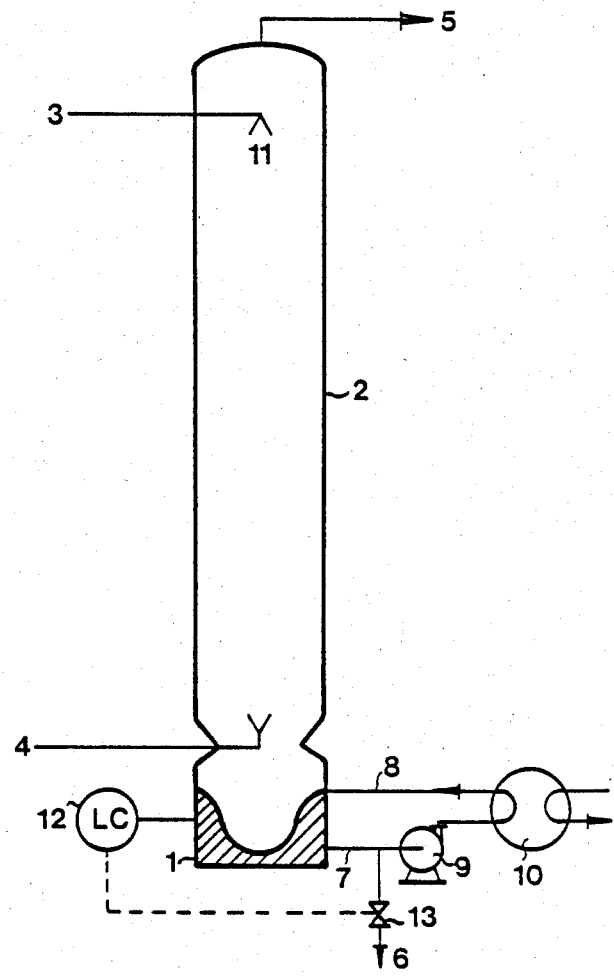

United States Patent [19]
Goorden et al.

[11] Patent Number: 4,652,675
[45] Date of Patent: Mar. 24, 1987

[54] PROCESS AND DEVICE FOR PURIFYING BENZOIC ACID

[75] Inventors: Josephus J. P. M. Goorden, Sittard; Antonius J. F. Simons, Geleen; Ludovicus A. L. Kleintjens, Stein, all of Netherlands

[73] Assignee: Stamicarbon B.V., Geleen, Netherlands

[21] Appl. No.: 795,641

[22] Filed: Nov. 6, 1985

[30] Foreign Application Priority Data

Nov. 23, 1984 [NL] Netherlands ............... 8403559

[51] Int. Cl.$^4$ .................................... C07C 51/42
[52] U.S. Cl. ......................................... 562/494
[58] Field of Search ........................ 562/495, 494

[56] References Cited

U.S. PATENT DOCUMENTS

| 2,255,421 | 9/1941 | Groll et al. | 562/494 |
| 4,227,018 | 10/1980 | Wolf et al. | 562/494 |
| 4,539,425 | 9/1985 | Kleintjens et al. | 562/412 |
| 4,547,587 | 10/1985 | Kleintjens et al. | 562/494 |

Primary Examiner—Paul J. Killos
Attorney, Agent, or Firm—Cushman, Darby & Cushman

[57] ABSTRACT

Process for purifying benzoic acid obtained by oxidation of toluene with a gas containing molecular oxygen, which purification is carried out at a pressure of at least 3 MPa by means of a supercritical extraction using a gas or gas mixture the critical temperature of which is lower than 435 K. The process being characterized in that the benzoic acid to be purified is supplied in a liquid state to a crystallizer in which the prevailing temperatures is below the solidification temperature of the benzoic acid and in which the benzoic acid is treated during and possibly after the crystallization process with the said gas or gas mixture.

12 Claims, 1 Drawing Figure

PROCESS AND DEVICE FOR PURIFYING BENZOIC ACID

The invention relates to a process for purifying benzoic acid obtained by oxidation of toluene with a gas containing molecular oxygen which purification is carried out at a pressure of at least 3 MPa by means of a supercritical extraction using a gas or gas mixture the critical temperature of which is lower than 435 K.

Such a process is known from the Netherlands patent application No. 8300008 laid open to public inspection. The process mentioned in that patent application is carried out substantially batchwise, the benzoic acid to be purified being extracted after the filling of a vessel required for that purpose, under supercritical conditions for a certain length of time using a gas or gas mixture the critical temperature of which is lower than 435 K. After this treatment the resulting purified benzoic acid is removed from said vessel, upon which the cycle can be repeated.

From the German patent specification No. 2460822 a process is known for the after-treatment of prilled benzoic acid with a heated inert gas, usually under atmospheric conditions, for the purpose of recovering the benzoic acid from a mixture of benzoic acid and diphenyls. The disadvantage of this process is that, in general, the duration of said after-treatment is long, while a separate column is required for the after-treatment.

A primary object of the invention is to provide a process for purifying benzoic acid that can be carried out continuously without requiring a separate after-treatment.

The invention consequently relates to a process for purifying benzoic acid obtained by oxidation of toluene with a gas containing molecular oxygen, which purification is carried out at a pressure of at least 3 MPa by means of a supercritical extraction using a gas or gas mixture the critical temperature of which is lower than 435 K. the process being characterized in that the benzoic acid to be purified is supplied in a liquid state to a crystallizer in which the prevailing temperature is below the solidification temperature of the benzoic acid and in which the benzoic acid is treated during and possibly after the crystallization process with the said gas or gas mixture.

By applying the process according to the invention a combined crystallization and extraction occurs, the impurities being removed already during the crystallization process.

Under the said process conditions the gas or gas mixture to be applied, such as for instance $SO_2$, $N_2O$, $NO_2$, NO, CO, $CH_4$, $N_2$, $CO_2$ and ethylene, is a so-called supercritical extractant. Supercritical means, by definition, that the process takes place at a temperature higher than or equal to the critical temperature of the gas or gas mixture and at a pressure higher than or equal to the critical pressure of the gas or gas mixture. For practical reasons preference is given to working in the optimum working range for supercritical extractants, which is bounded by a $T_r$ of 0.9-1.5 at a $P_r \geq 0.9$, where $T_r$ is the reduced temperature, which is by definition the ratio between the process temperature and the critical temperature (both of them expressed in K), and $P_r$ the reduced pressure, which is by definition the ratio between the process pressure and the critical pressure. Beyond this working range, to lower $T_r$ and/or $P_r$ values, minor changes in pressure and/or temperature may result in a strong decrease of the dissolving power of the extractant.

The invention is particularly suitable for purifying benzoic acid by means of a continuous process if the crystallization is done by prilling. In that process benzoic acid particles with certain small dimensions can be made, which have a large area of contact compared with for instance flakes and, moreover, a narrow particle size distribution, which facilitates the extraction of impurities. When crystallization is effected counter-currently to a supercritical extractant, good advantage can be taken of another property of supercritical fluids, viz. a high specific gravity in respect of gas. Thus, on the one side, the falling velocity of the benzoic acid particle is strongly retarded, but on the other side the heat and mass transfer from the particle to the extractant is strongly increased. The process according to the invention can consequently be carried out in one apparatus and continuously while meeting the criteria for optimum crystallization as well as for optimum extraction.

The supercritical extractant used is preferably a gas or gas mixture consisting of $CO_2$ and/or ethylene. $CO_2$ is used in particular, because it is non-toxic, non-flammable, not harmful to the environment, and cheap.

The amount of gas or gas mixture used in a process according to the invention can be chosen, for instance, between 1 and 500 $Nm^3$ (NPT) gas per kg benzoic acid and is determined by the degree of purification aimed at.

The temperature to be applied in a process according to the invention must not be higher than the solidification temperature of the benzoic acid. The lower temperature limit is determined on the one side because the $T_r$ must preferably not fall below 0.9 and will on the other side for practical reasons not be taken below the ambient temperature.

The process-pressure to be applied in the process according to the invention will at least have to be 0.9 time the critical pressure of the extractant to be applied, but will advantageously have a value of 3-300 MPa.

After the extraction the purified solid benzoic acid must be removed from the extractor. The processes known for this removal are usually batchwise in design. This is due to the fact that the semicontinuous or continuous transportation of the solid substance to and from the high-pressure section in which the supercritical extraction is carried out is a mostly insuperable technical obstacle.

In the present state of the art transportation systems are known for this purpose, in which connection reference is made to VDI-Berichten No. 409, 1981, and US-A-No. 3,190,701. The possibilities for solids removal systems are closely related to the morphology and the running characteristics, the hardness and brittleness of the solid, which may result in wearing of parts like valves and other moving parts.

Moreover, care must be taken that, before its removal to an environment of atmospheric pressure, the extracted solid phase is cleared of the extract phase, which is laden with the extracted impurities. To this end, for instance, flushing or washing with pure extractant will be necessary in practice. This will result in a loss of extractant, as well as in extra compression costs of extractant to be newly supplied.

A further object of the invention now is also to provide a process for a continuous transportation of the purified benzoic acid with a drastic reduction of the loss of extractant. This is achieved in that the crystals of purified benzoic acid thus obtained are remelted at least partly and are carried off in at least partly liquid form.

By applying the process according to the invention a supercritical extraction of solid benzoic acid is carried out while the objections inherent in the transportation of a solid substance are avoided by the supply and removal of the substance in at least partly liquid form.

As the solubility of the extractant in liquid benzoic acid is lower than the volume fraction of empty space between the crystals occupied by the extractant in the removal of the benzoic acid, a substantial reduction of the loss of extractant is achieved while at the same time, the benzoic acid need no longer be cleared, before its removal, of the impurities-laden extract phase, for instance by flushing or washing with pure extractant.

The re-melting of the benzoic acid crystals can advantageously be effected by keeping part of the liquid material carried off in circulation over the bottom section of the extractor. The heat required for the melting of the crystals is supplied to the circulated flow through heat exchange with this flow. In order to come to a proper heat transfer between the circulated flow and the crystals and in order to take care that a substantially liquid phase is drained off, preference is given to the recirculated flow, as well as the flow of liquid material carried off, being tangentially supplied to, respectively carried off from, the bottom section of the extractor. This results in the presence of a vortex in the bottom section. It is not necessary to carry off a complete melt from the bottom section. This depends on the way in which later in the process the liquid phase is processed. The chosen solids concentration in the circulated flow is then preferably such that it is nowhere in excess of 20% (wt). because otherwise clogging may occur.

The invention is further elucidated by means of the attached drawing without restricting the invention to it. FIG. 1 represents a vertical section of the device.

Melting section (bottom section) 1 of crystallizer/extractor 2 is provided with a tangential outlet 7, a tangential feed 8 and a drain 6.

In the device in operation for purifying benzoic acid the liquid benzoic acid is supplied through feed 3 and spray nozzle 11 and the supercritical extractant through feed 4. The extract phase is carried off through 5, while the pure benzoic acid crystals find their way to bottom section 1. Bottom section 1 contains a suspension of the benzoic acid in its own melt. This suspension is pumped continuously by pump 9 through heater 10 from outlet 7 to feed 8.

Via drain 6 part of the circulating suspension, equalling the amount of benzoic acid supplied to the extractor, is withdrawn from the system, which can be controlled preferably via a level control 12 controlling the discharge via control valve 13.

EXAMPLE

To a column as shown in FIG. 1, 0.168 m in diameter and 2 m high, 100 kg/h benzoic acid contaminated with diphenyls is supplied at a temperature of 125° C. The impurities contained in this benzoic acid consist of 0.02% (wt) diphenyl oxide, 0.02% (wt) 2-methyldiphenyl and 0.16% (wt) 3- and 4-methyldiphenyl. The benzoic acid is supplied through a perforated plate in the top of the column, in which perforated plate 100 holes of 0.4 mm have been made. The extractant used is $CO_2$, which is fed at the bottom of the column in an amount of 1155 kg/h at a temperature of 35° C. The whole is under a pressure of 10 MPa. At the top of the column the $CO_2$, now laden with the extracted impurities, is carried off at a temperature of 37.5° C. The purified benzoic acid is melted in the melting device in the bottom of the extraction/crystallization column and carried off from the melting device at a temperature of 125° C. The impurities still contained in this purified benzoic acid consist of only 0.0003% (wt) 3- and 4-methyldiphenyls, the purified benzoic acid being of the pharmacopeia grade according to USP-20.

We claim:

1. Continuous process for purifying benzoic acid obtained by oxidation of toluene with a gas containing molecular oxygen by supercritical extraction, said process comprising the steps of:
   (a) supplying liquid benzoic acid which is to be purified to a crystallizer, said crystallizer being operated at a pressure of least 3 MPa, and at a temperature below the solidification temperature of the benzoic acid; and
   (b) treating the benzoic acid during and possibility after the crystallization process with a gas or gas mixture, the critical temperature of which is lower than 435° K.

2. Process according to claim 1, characterized in that the crystallizer is a prilling tower.

3. Process according to claim 1, characterized in that the gas or gas mixture consists of $CO_2$, ethylene or a mixture thereof.

4. Process according to claim 1, characterized in that the gas flow rate applied is 1 to 500 $Nm^3$ (NPT) gas per kg benzoic acid per hour.

5. Process according to claim 1, characterized in that in the crystallizer a pressure of 3–300 MPa is maintained.

6. Process according to claim 1, characterized in that after extraction the purified benzoic acid crystals thus obtained are at least partly melted and are carried off in at least partly liquid form.

7. Process according to claim 6, characterized in that at least part of the liquid material drained is recirculated to the extractor via a heat exchanger.

8. Process according to claim 7, characterized in that the recirculated flow is fed tangentially into the extractor.

9. Device suitable for purifying benzoic acid using the process according to any one of the above claims, resistant against a pressure of at least 3 MPa, consisting of: an extraction-crystallization column provided at its top with a feeder for liquid benzoic acid and a drain for extract phase, provided at its bottom with a feeder for an extractant, as well as with a melting device for re-melting the purified benzoic acid crystals, which melting device is provided with a drain for completely or partly melted benzoic acid.

10. Device according to claim 9, characterized in that the melting device is connected via the drain to a pump connected on its delivery side with a heat exchanger, which is connected in its turn with a feeder to the melting device for the recirculation of completely or partly remelted benzoic acid.

11. Device according to claim 10, characterized in that the melting device is provided with a feeder fetted tangentially for the recirculated flow.

12. Device according to claim 9, characterized in that the melting device is provided with a level control controlling the benzoic acid drain from the device by means of a control valve.

* * * * *